United States Patent
Marshall et al.

(10) Patent No.: US 10,006,857 B2
(45) Date of Patent: Jun. 26, 2018

(54) LASER-SCATTER MEASUREMENT INSTRUMENT HAVING CAROUSEL-BASED FLUID SAMPLE ARRANGEMENT

(71) Applicant: BacterioScan LTD, MP Western Galilee (IL)

(72) Inventors: Dana A. Marshall, St. Louis, MO (US); Dan Vadim Regelman, Kiryat Bialik (IL)

(73) Assignee: Bacterioscan Ltd., MP Western Galilee (IL)

( * ) Notice: Subject to any disclaimer, the term of this patent is extended or adjusted under 35 U.S.C. 154(b) by 68 days.

(21) Appl. No.: 15/005,321

(22) Filed: Jan. 25, 2016

(65) Prior Publication Data

US 2016/0216204 A1    Jul. 28, 2016

Related U.S. Application Data

(60) Provisional application No. 62/107,931, filed on Jan. 26, 2015.

(51) Int. Cl.
*G01N 21/51* (2006.01)
*G01N 21/03* (2006.01)

(52) U.S. Cl.
CPC ......... *G01N 21/51* (2013.01); *G01N 21/0303* (2013.01); *G01N 2021/513* (2013.01);
(Continued)

(58) Field of Classification Search
CPC ............... G01N 21/51; G01N 21/0303; G01N 2021/513; G01N 2201/0231; G01N 2201/0415; C12Q 1/06
See application file for complete search history.

(56) References Cited

U.S. PATENT DOCUMENTS 3,627,424 A   12/1971   Dorman et al.
3,713,775 A    1/1973   Schmitz
(Continued)

FOREIGN PATENT DOCUMENTS

DE   10128978   12/2002
EP    0320154    6/1989
(Continued)

OTHER PUBLICATIONS

Murray, et al. "Light-scattering methods for antibiotic sensitivity tests", J Clin Pathol, 1980, vol. 33, pp. 995-1001, 8 pages.
(Continued)

*Primary Examiner* — Gautam Prakash
(74) *Attorney, Agent, or Firm* — Nixon Peabody LLP

(57) ABSTRACT

An instrument determines a concentration of bacteria in a plurality of fluid samples, and comprises a housing, a rotatable platform, a plurality of fluid containers, a light source, a sensor, and a motor. The rotatable platform is within the housing. The fluid containers are located on the rotatable platform. Each fluid container holds a corresponding one of the plurality of fluid samples, and has an input window and an output window. The light source provides an input beam for transmission into the input windows of the fluid containers and through the corresponding fluid samples. The input beam creates a forward-scatter signal associated with the concentration of bacteria. The motor rotates the rotatable platform so that the input beam sequentially passes through each fluid sample. A sensor within the housing detects the forward-scatter signal exiting from the output window associated with the fluid sample receiving the input beam.

12 Claims, 10 Drawing Sheets

(52) U.S. Cl.
CPC ............... *G01N 2201/0231* (2013.01); *G01N 2201/0415* (2013.01)

(56) References Cited

U.S. PATENT DOCUMENTS

| | | | |
|---|---|---|---|
| 3,832,532 | A | 8/1974 | Praglin et al. |
| 3,928,140 | A | 12/1975 | Wyatt et al. |
| 4,066,360 | A | 1/1978 | Breddin et al. |
| 4,101,383 | A | 7/1978 | Wyatt et al. |
| 4,113,386 | A | 9/1978 | Lepper, Jr. |
| 4,119,407 | A | 10/1978 | Goldstein et al. |
| 4,265,538 | A | 5/1981 | Wertheimer |
| 4,577,970 | A | 3/1986 | Meserol |
| 4,754,613 | A | 7/1988 | Brito |
| 4,874,102 | A | 10/1989 | Jessop |
| 4,895,446 | A | 1/1990 | Maldari et al. |
| 5,139,031 | A | 8/1992 | Guirguis |
| 5,187,368 | A | 2/1993 | Galante et al. |
| 5,212,667 | A | 5/1993 | Tomlinson, Jr. et al. |
| 5,351,118 | A | 9/1994 | Spinell |
| 5,616,923 | A | 4/1997 | Rich et al. |
| 5,693,944 | A | 12/1997 | Rich |
| 5,969,814 | A | 10/1999 | Barber |
| 5,989,499 | A | 11/1999 | Catanzariti |
| 6,091,483 | A | 7/2000 | Guirguis |
| 6,230,045 | B1 | 5/2001 | Hoogenraad et al. |
| 6,333,008 | B1 | 12/2001 | Leistner et al. |
| 6,573,992 | B1 | 6/2003 | Drake |
| 6,861,230 | B1 | 3/2005 | Murphy et al. |
| 7,430,046 | B2 | 9/2008 | Jiang et al. |
| 7,961,311 | B2 | 6/2011 | Weichselbaum et al. |
| 8,339,601 | B2 | 12/2012 | Weichselbaum et al. |
| 2003/0048433 | A1 | 3/2003 | Desjonqueres |
| 2004/0070756 | A1 | 4/2004 | Rastopov |
| 2004/0185552 | A1 | 9/2004 | Grinner et al. |
| 2004/0238746 | A1 | 12/2004 | Dreyer et al. |
| 2005/0064582 | A1* | 3/2005 | Wittwer et al. ........ B01L 3/5082 435/287.2 |
| 2005/0148085 | A1 | 7/2005 | Larsen |
| 2006/0063146 | A1 | 3/2006 | Larsen et al. |
| 2006/0109476 | A1 | 5/2006 | Werner et al. |
| 2006/0256338 | A1 | 11/2006 | Gratton et al. |
| 2007/0155017 | A1 | 7/2007 | Wyatt |
| 2007/0159619 | A1 | 7/2007 | Chu et al. |
| 2007/0195324 | A1 | 8/2007 | Adams et al. |
| 2007/0206203 | A1 | 9/2007 | Trainer |
| 2007/0211251 | A1 | 9/2007 | Weischselbaum |
| 2007/0253042 | A1 | 11/2007 | Szarvas |
| 2008/0106737 | A1 | 5/2008 | Weichselbaum et al. |
| 2008/0293091 | A1 | 11/2008 | Kanipayor |
| 2010/0068755 | A1 | 3/2010 | Walsh |
| 2010/0277734 | A1 | 11/2010 | Weischselbaum |
| 2013/0089476 | A1 | 4/2013 | Weichselbaum et al. |
| 2013/0309686 | A1* | 11/2013 | Stimpson ................. C12Q 1/04 435/6.15 |

FOREIGN PATENT DOCUMENTS

| | | |
|---|---|---|
| EP | 1136563 | 9/2001 |
| GB | 1515681 | 6/1978 |
| GB | 2412166 | 9/2005 |
| WO | WO 00/09981 | 2/2000 |
| WO | WO 00/66763 | 11/2000 |
| WO | WO 2006/018839 | 2/2006 |
| WO | WO 2013/070948 | 5/2013 |
| WO | WO 2013/153371 | 10/2013 |

OTHER PUBLICATIONS

International Search Report, PCT/IB2016/050364, dated Apr. 21, 2016 (3 pages).
Written Opinion of the International Searching Authority, PCT/IB2016/050364, dated Apr. 21, 2016 (5 pages).

* cited by examiner

LASER-SCATTER MEASUREMENT INSTRUMENT HAVING CAROUSEL-BASED FLUID SAMPLE ARRANGEMENT

RELATED APPLICATIONS

The present application claims priority to U.S. Provisional Application Ser. No. 62/107,931, filed Jan. 26, 2015, titled "Multi-Sample Laser-Scatter Measurement Instrument With Incubation Feature," which is herein incorporated by reference in its entirety.

COPYRIGHT

A portion of the disclosure of this patent document may contain material which is subject to copyright protection. The copyright owner has no objection to the facsimile reproduction by anyone of the patent disclosure, as it appears in the Patent and Trademark Office patent files or records, but otherwise reserves all copyright rights whatsoever

FIELD OF THE INVENTION

The present invention relates generally to the field of measurements of biological liquid samples. Specifically, the present invention relates to systems and method for determining whether bacteria are present in a liquid sample and, if so, for determining the effect of chemoeffectors on the bacteria within the liquid sample.

BACKGROUND OF THE INVENTION

Many applications in the field of analytical research and clinical testing utilize methods for analyzing liquid samples. Among those methods are optical measurements that measure absorbance, turbidity, fluorescence/luminescence, and optical scattering measurements. Optical laser scattering is one of the most sensitive methods, but its implementation can be very challenging, especially when analyzing biological samples in which suspended particles are relatively transparent in the medium.

One particle that often requires evaluation within a liquid is bacteria. The presence of bacteria is often checked with biological liquids, such as urine, amniotic, pleural, peritoneal and spinal liquids. In a common analytical method, culturing of the bacteria can be time-consuming and involves the use of bacterial-growth plates placed within incubators. Normally, laboratory results take may take a day or several days to determine whether the subject liquid is infected with bacteria and the type of bacteria.

Quantification of bacteria, yeast, and other organisms in fluid can be useful for medical diagnosis, drug development, industrial hygiene, food safety, and many other fields. Measurement of light scattering and absorption in samples is a known method for approximating the concentration of organisms. For example, techniques for detecting and counting bacteria are generally described in U.S. Pat. Nos. 7,961, 311 and 8,339,601, both of which are commonly owned and are herein incorporated by reference in their entireties.

Accordingly, there is a need for an improved systems and methods that quickly determine whether bacteria is present in the fluid sample and determine the effect of chemoeffectors on a fluid sample. There is also a need for an improved systems and methods that more quickly determine the type of bacteria after the presence of bacteria is determined.

SUMMARY OF THE INVENTION

The present invention is directed to an instrument for taking measurements of organism concentration in multiple fluid samples or in a single fluid sample as a production tool for microbiology. The instrument may hold multiple, individually-loaded, independent fluid samples and determine bacteria concentration of each sample via a forward-scattering signal. Or the instrument may hold a single fluid sample in multiple wells, which contain one or more different chemoeffectors to act on the single fluid. Thus, the effects of a chemoeffector (or concentrations of chemoeffectors) on the bacteria concentration in each fluid sample can be based on forward-scattering signals of the fluid sample over a period of time.

In one aspect, the instrument determines a concentration of bacteria in a plurality of fluid samples, and comprises a housing, a rotatable platform, a plurality of fluid containers, a light source, a sensor, and a motor. The rotatable platform is within the housing. Each of the plurality of fluid containers is coupled to the rotatable platform. Each of the fluid containers holds a corresponding one of the plurality of fluid samples. Each of the fluid containers has an input window and an output window. The light source is within the housing and provides an input beam for transmission into the input windows of the fluid containers and through the corresponding fluid samples. The input beam creates a forward-scatter signal associated with the concentration of bacteria. The motor rotates the rotatable platform so that the input beam sequentially passes through each of the plurality of fluid samples. At least one sensor within the housing detects the forward-scatter signal exiting from the output window associated with the fluid sample receiving the input beam.

In yet a further aspect, the present invention is a method of determining the concentration of bacteria in a plurality of fluid samples. The method includes placing each of the fluid samples in a corresponding one of a plurality of fluid chambers located within a cuvette. Each fluid chamber has a first window for receiving an input beam and a second window for transmitting a forward-scatter signal caused by the input beam. The method further includes registering the cuvette on a rotatable platform associated with an optical measuring instrument, incrementally rotating the rotatable platform so as to sequentially pass the input beam through each of the fluid samples, and in response to passing the input beam through each of the fluid samples, measuring a first forward-scatter signal for each of the fluid samples.

Alternatively, the present invention is an optical measuring instrument for determining a concentration of bacteria in fluid samples. The instrument comprises a housing, a door, a light source, and a rotatable platform. The door is coupled to the housing. The door includes a door platform that extends inwardly into the housing when the door is positioned in a closed state. The light source and a sensor measure an optical signal from the fluid samples. The optical scatter signal is associated with the concentration of bacteria. The rotatable platform is coupled to the door platform. The rotatable platform receives one or more cuvettes that hold the fluid samples. The rotatable platform sequentially moves each of the fluid samples into a testing position for measurement by use of the light source and the sensor.

In yet another aspect, the present invention is an optical measuring instrument for determining a concentration of bacteria in a plurality of fluid samples. The instrument includes a cuvette, a first light source, a first sensor, a second light source, and a second sensor. The cuvette has a plurality of optical chambers for receiving a respective one of the plurality of fluid samples. Each of the optical chambers is at least partially formed by an entry window for allowing transmission of an input beam through the respective fluid sample and an exit window for transmitting an optical signal caused by the bacteria within the respective fluid sample. A first group of the optical chambers contains a first group of the fluid samples. A second group of the optical chambers contains a second group of the fluid samples. The first group of the optical chambers is located on a first locus having a first radius, and the second group of the optical chambers is located on a second locus having a second radius. The first radius is different from the second radius. The first light source produces a first input beam. The first sensor receives a first optical signal that is responsive to a bacterial concentration in the fluid sample and the first input beam. The first light source and the first sensor develop a first series of optical signals that are used for determining the concentration of bacteria within each fluid sample of the first group of fluid samples. The second light source produces a second input beam. The second sensor receives a second optical signal that is responsive to a bacterial concentration in the fluid sample and the second input beam. The second light source and the second sensor develop a second series of optical signals that are used for determining the concentration of bacteria within each fluid sample of the second group of fluid samples.

In another aspect, the present invention is a cuvette for use in an optical measuring instrument for determining a characteristic of a plurality of fluid samples. The cuvette includes a plurality of optical chambers for receiving a respective one of the plurality of fluid samples. Each of the optical chambers includes an entry window for allowing transmission of an input beam through the respective fluid sample and an exit window for transmitting an optical signal caused by the respective fluid sample. A first group of the optical chambers is located on a first locus having a first radius, while a second group of the optical chambers is located on a second locus having a second radius. The first radius being different from the second radius.

Additional aspects of the invention will be apparent to those of ordinary skill in the art in view of the detailed description of various embodiments, which is made with reference to the drawings, a brief description of which is provided below.

Figure 1:
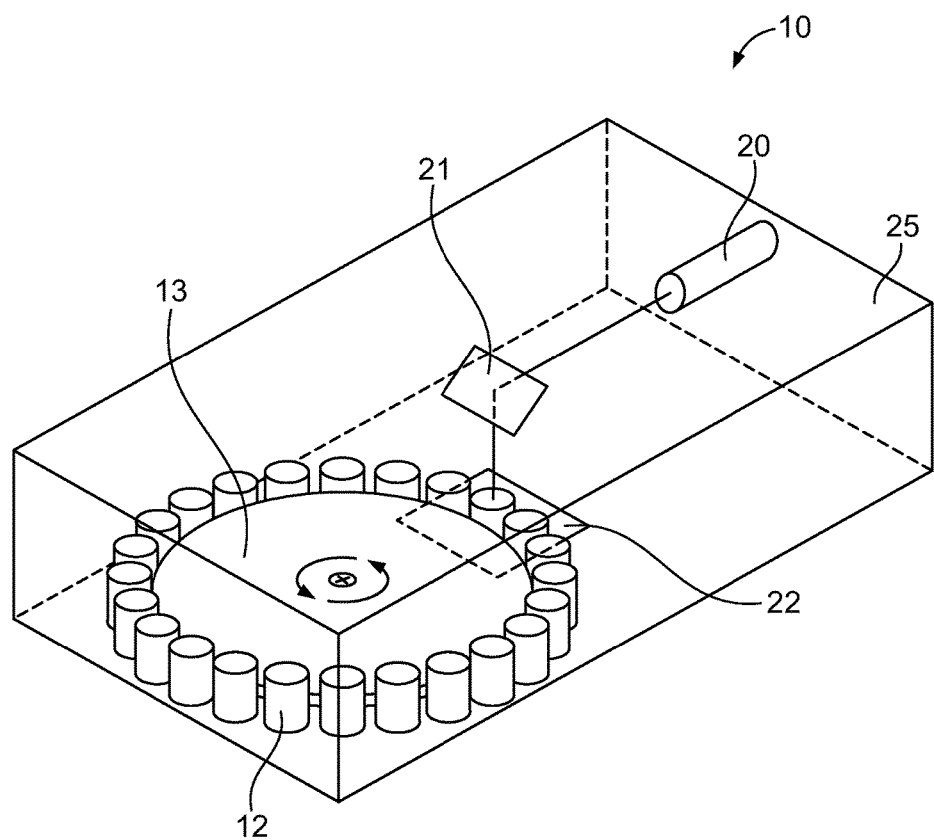
FIG. 1 schematically illustrates an optical-measuring instrument that is capable of testing fluid samples on a rotational platform.

While the invention is susceptible to various modifications and alternative forms, specific embodiments will be shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

DETAILED DESCRIPTION

The drawings will herein be described in detail with the understanding that the present disclosure is to be considered as an exemplification of the principles of the invention and is not intended to limit the broad aspect of the invention to the embodiments illustrated. For purposes of the present detailed description, the singular includes the plural and vice versa (unless specifically disclaimed); the words "and" and "or" shall be both conjunctive and disjunctive; the word "all" means "any and all"; the word "any" means "any and all"; and the word "including" means "including without limitation."

FIG. 1 illustrates a general functional representation of an optical measuring instrument 10 that has one or more light input beams that are fixed in position. Multiple sample chambers 12 (e.g., cuvettes) are held by a rotatable platform 13 that moves each sample into the path of the light input beam within the optical measuring instrument 10. The light is developed by a light source, such as a laser 20 and may reflect off a turning mirror 21 before being transmitted through the fluid sample within the sample in the cuvette 12. A sensor 22 receives the optical signal (e.g., a forward-scatter signal), which is then processed/analyzed to determine the presence and/or growth of bacteria over a period of time. The optical measuring instrument 10 may incorporate conductive heating and cooling, or radiant heating from an optical or infrared source for control of the temperature of the fluid samples, thereby providing proper incubation. These features are described in detail below with reference to FIGS. 2-7.

Figure 2:
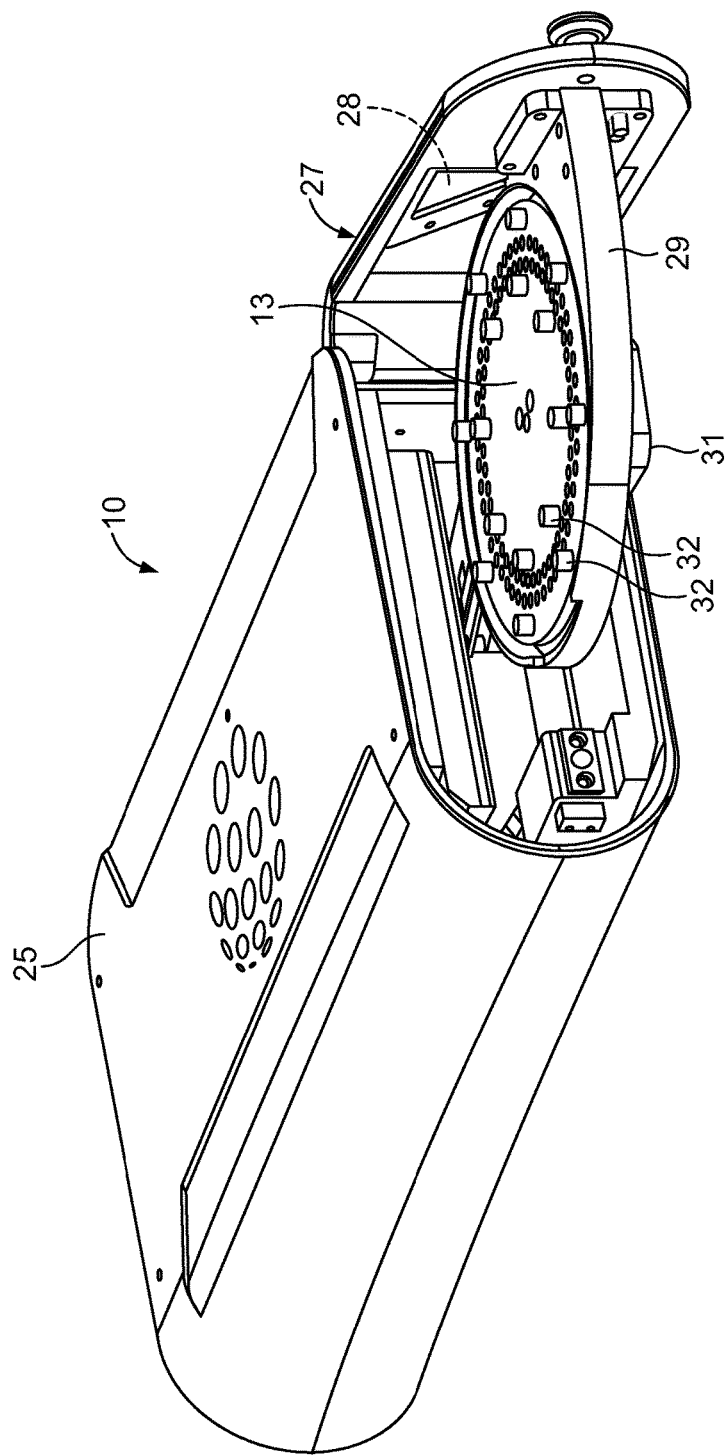
FIG. 2 illustrates one detailed embodiment of the optical-measuring instrument of FIG. 1 that uses the rotational platform.

FIG. 2 illustrates the instrument 10 that includes a housing 25 with a door 27 that opens and closes on one end of the housing 25. The door 27 includes a display device 28 that displays various pieces of information about the instrument 10. The display device 28 may provide information regarding the test status (e.g., the current temperature within the instrument 10 or the remaining minutes left in the test), the fluid samples, and/or the test protocol being used for the fluid samples, (e.g., time and temperature). Preferably, the display device 28 also includes an associated touchscreen input (or a different set of input buttons can be provided) that allows a user to perform some of the basic functions of the instrument 10, such as a power on/off function, a door open/close function, a temperature increase/decrease function, etc.

Figure 6A:
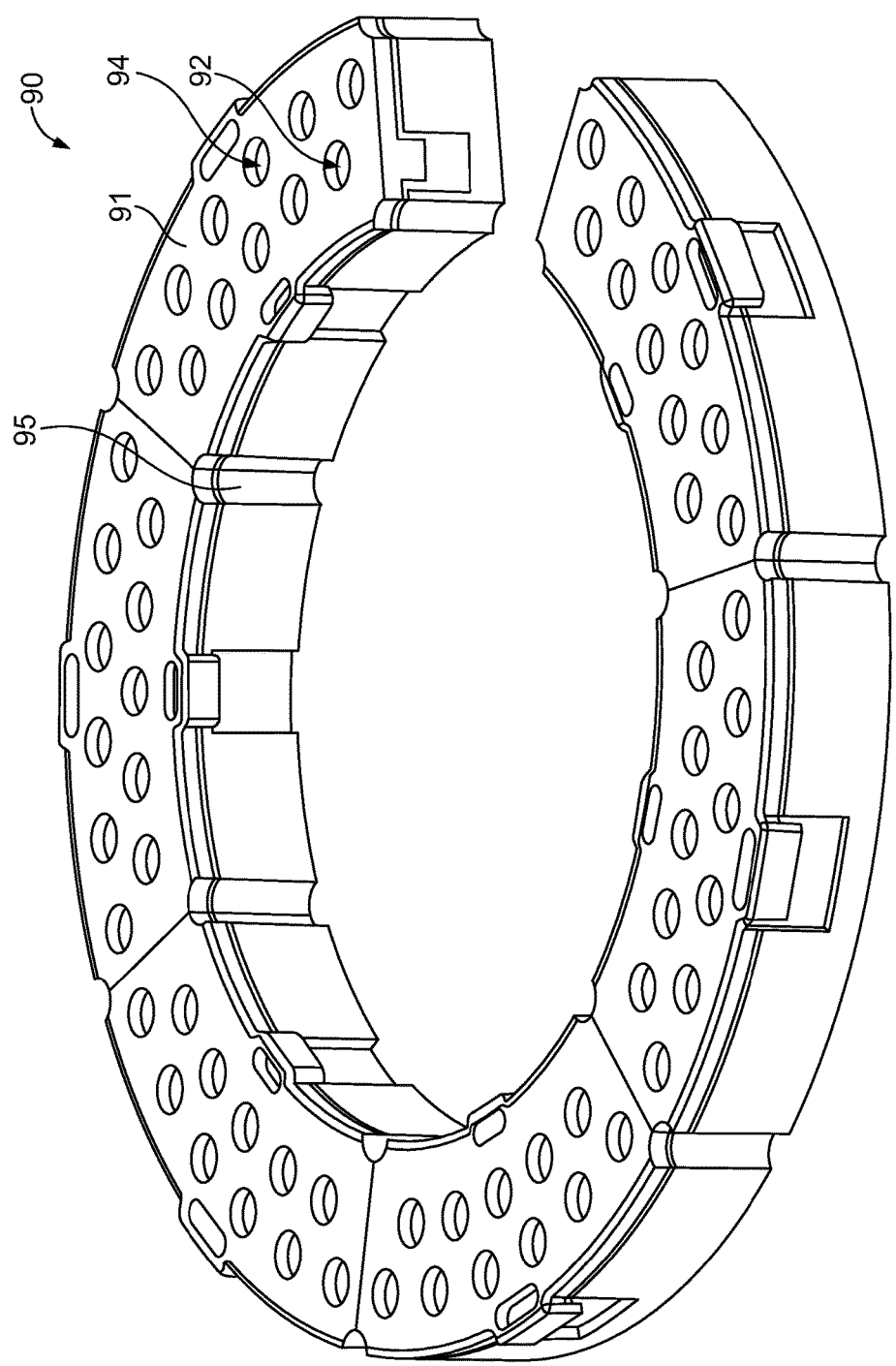
FIG. 6A illustrates a perspective view of a cuvette assembly that fits on the rotational platform of the instruments of FIGS. 1-5.
Figure 6B:
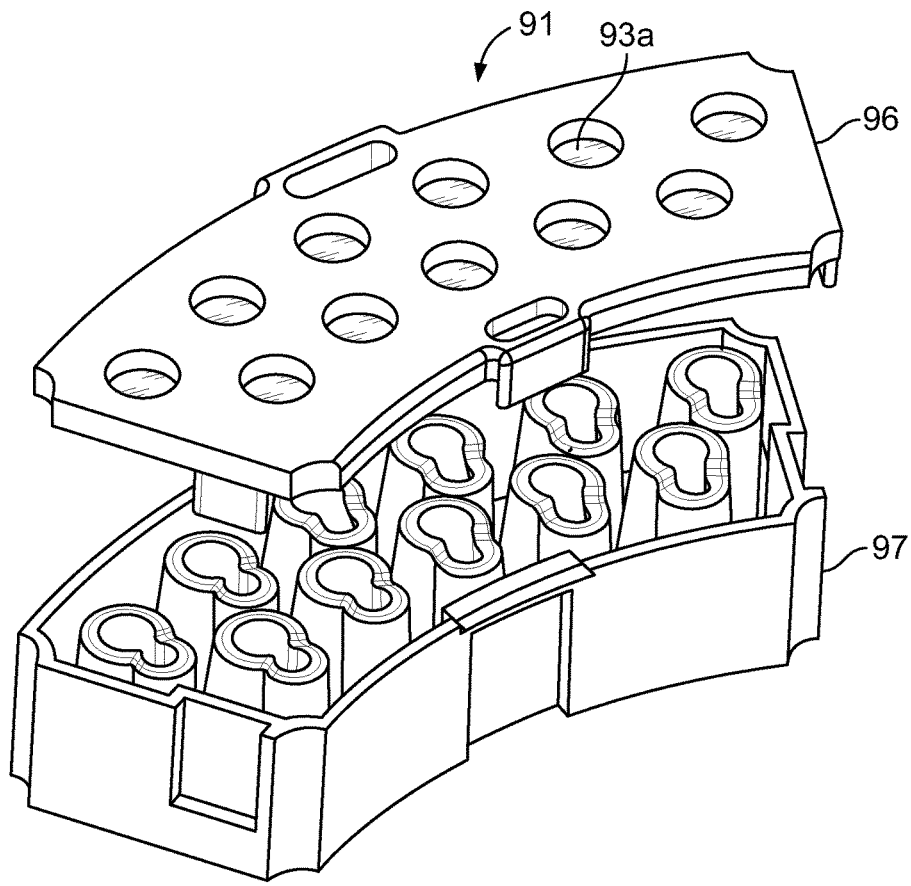
FIG. 6B illustrates an exploded perspective view of a single cuvette of the cuvette assembly of FIG. 6A.
Figure 6C:
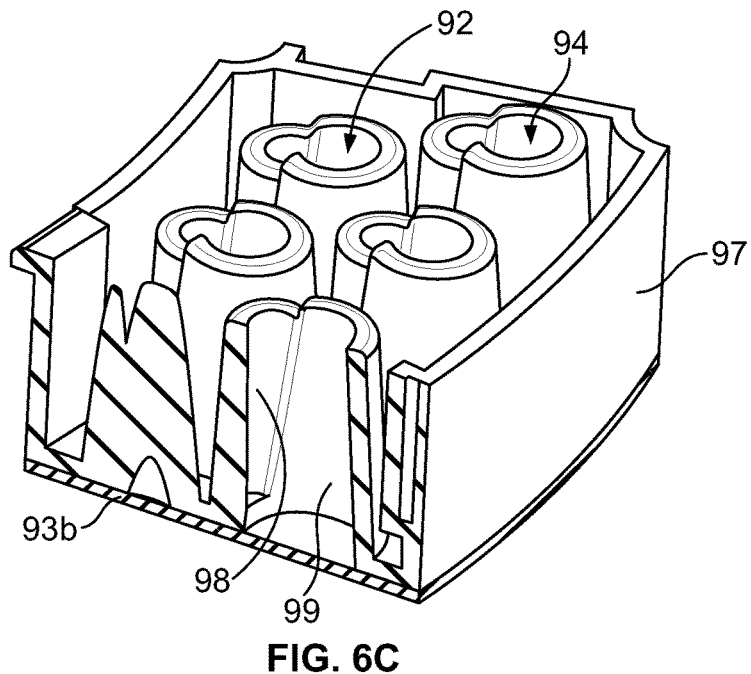
FIG. 6C is a partial cross-sectional view of the main body of the single cuvette of FIG. 6B.

The door 27 includes a door platform 29 that supports the rotatable platform 13 for receiving the plurality of individual cuvettes 12 or a cuvette assembly comprised of a plurality of cuvettes (e.g., the cuvette assembly 90 shown in FIGS. 6A-6C). As such, the rotatable platform 13 is a carousel-like structure for transporting individual, discrete fluid samples through a test protocol involving the repetitive transmission of an input beam from the laser(s) 20 for measuring the forward scatter signal over a period of time to monitor a change in bacterial concentration. To hold the fluid samples in a fixed orientation, the rotatable platform 13 includes a plurality of registration posts 32 that register the cuvettes on the rotatable platform 13. Furthermore, the rotatable platform 13 includes a plurality of openings that are aligned with the cuvettes and permit transmission of the light input beams associated with the testing. A carousel-position sensor 33 is located on or within the door platform 29 for sensing the circumferential location of the rotatable platform 13. The door 27 has seals and/or gaskets around it so that the instrument 10 provides a light-tight enclosure to ensure proper signal detection by the sensors 22.

Figure 3:
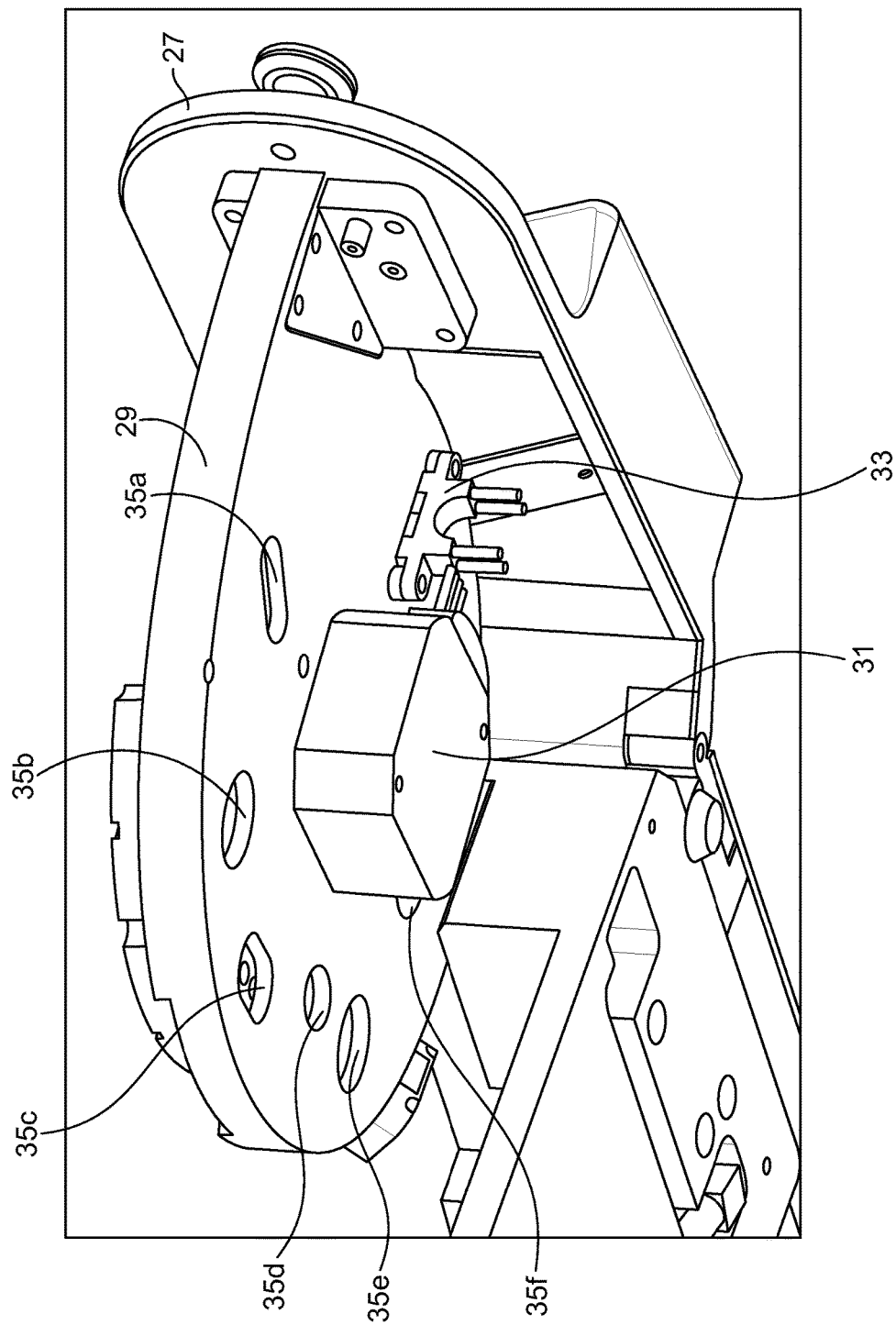
FIG. 3 illustrates an underside perspective view of the door platform of the instrument of FIG. 2.

FIG. 3 illustrates a lower view of the door platform 29. A stepper motor 31 for rotating the rotatable platform 13 is positioned below and attached to the door platform 29. The stepper motor 31 provides the carousel-like movement to the rotatable platform 13 through a shaft that extends through the door platform 29. The door platform 29 also includes a plurality of openings 35 that serve different purposes. For example, some of the openings 35*b*, 35*c*, and 35*e* are for receiving heat energy to maintain the rotatable platform 13 at a desirable temperature and encourage bacterial incubation. As discussed below with reference to FIG. 4, the heat energy is transmitted to the rotatable plate 13 from a plurality of lamps 44 located on the lower portion of the instrument 10 within the housing 25. Another one of the openings 35*d* is for transmitting infrared radiation from the rotatable platform 13 to a temperature sensor located on the lower portion of the instrument 10. Two of the openings 35*a* and 35*f* are for transmitting to the sensors 22 the forward scatter signal caused by the bacterial concentration within the fluid sample in response to the input beam laser 20 being transmitted into the fluid samples. The door platform 29 can include more or less openings 35 depending on whether more or less functions are required from the bottom side of the door platform 29.

Figure 4:
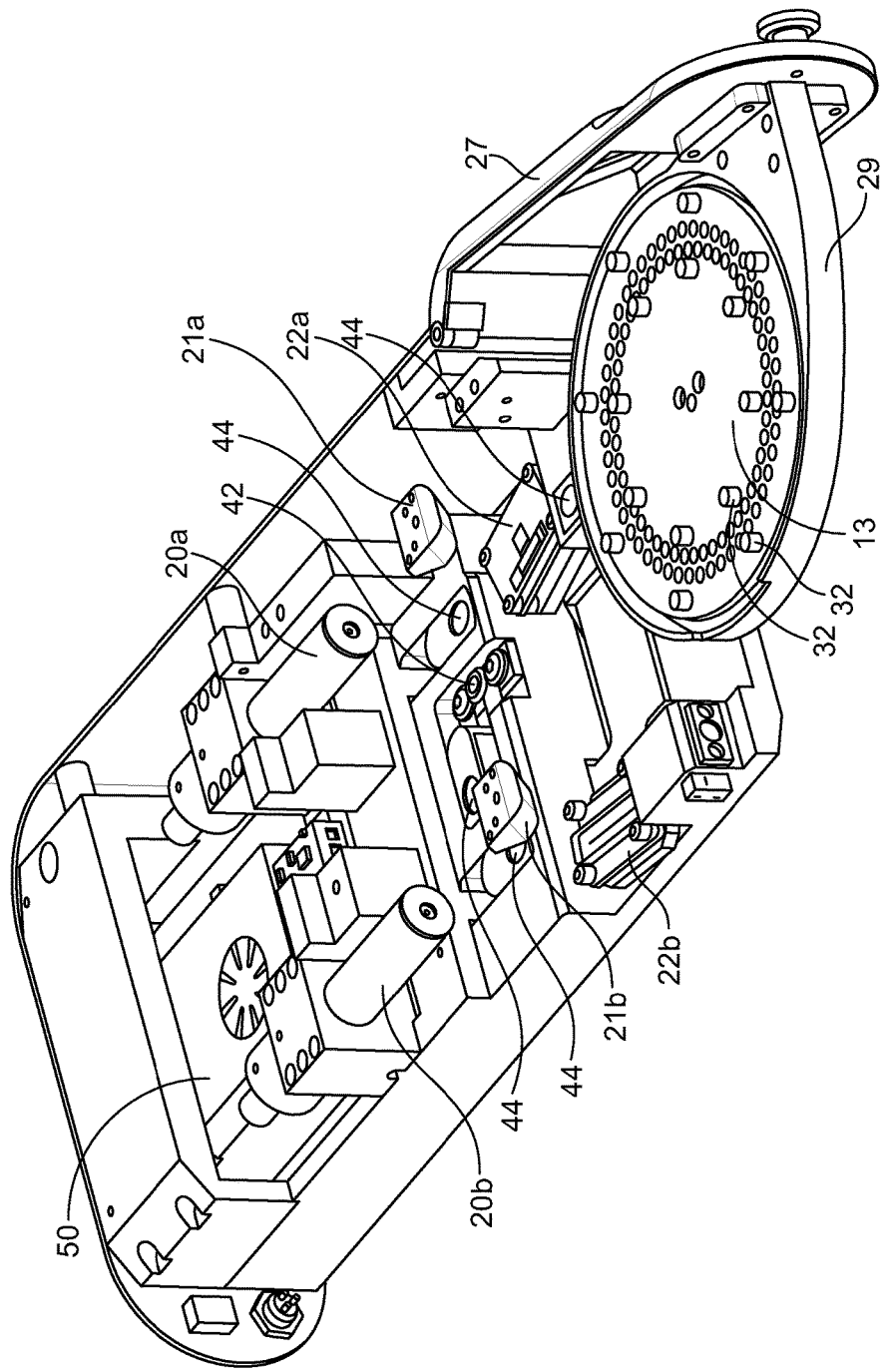
FIG. 4 illustrates a front perspective view of the instrument of FIG. 2 with a portion of the housing removed and the door opened, such that the rotational platform is in the loading position.
Figure 5:
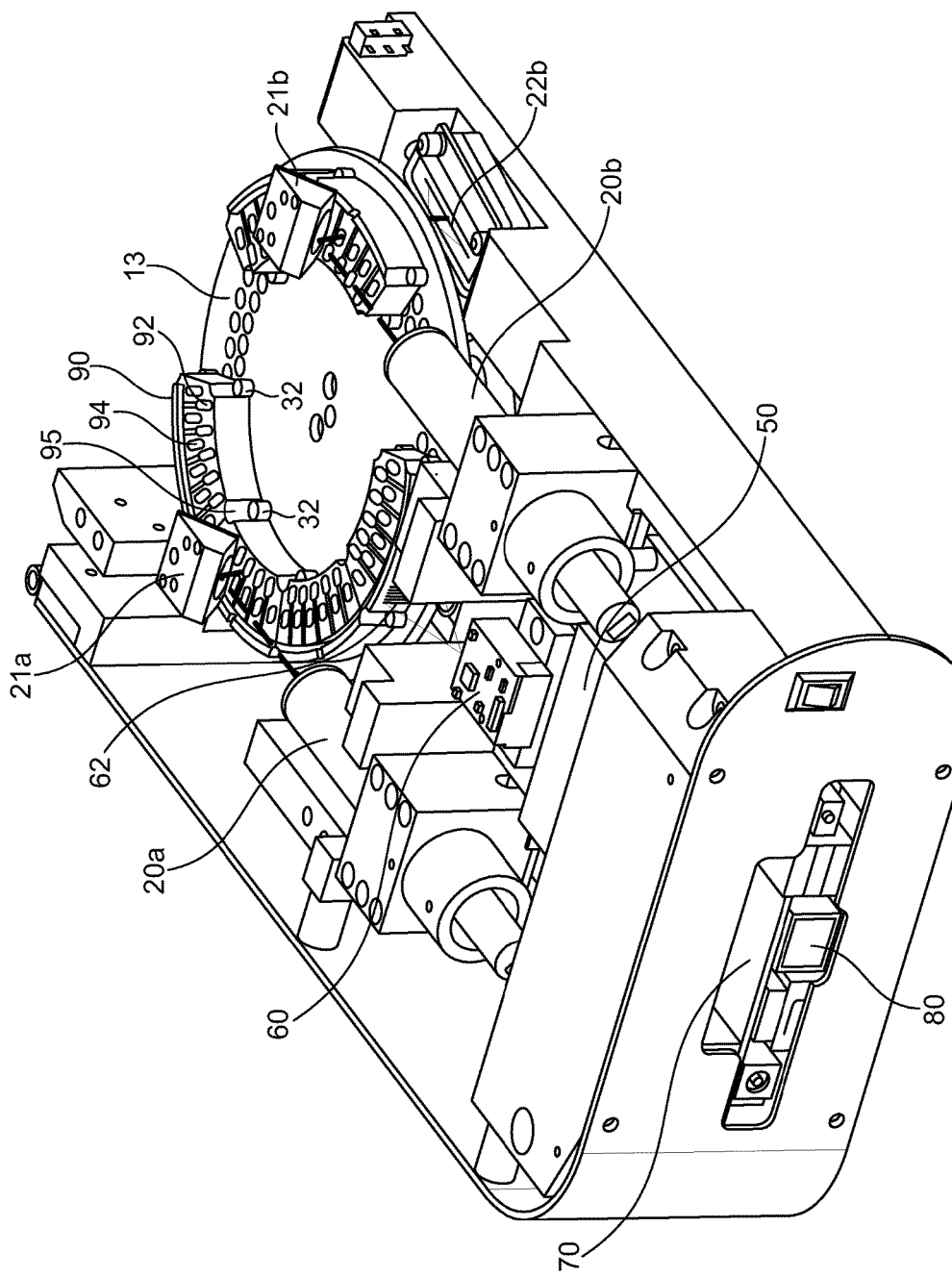
FIG. 5 illustrates a rear perspective view of the instrument of FIG. 2 with a portion of the housing removed and the door and the rotational platform in the operational or closed position.

FIGS. 4 and 5 illustrate the arrangement of the internal components of the instrument 10. A first laser 20*a* is designed to provide input energy for a first group of fluid samples, while the second laser 20*b* is designed to provide input energy for a second group of fluid samples. The input energy from the first laser 20*a* reflects from a first mirror 21*a* and is transmitted downwardly toward the first sensor 22*a*. The input energy from the second laser 20*b* reflects from a second mirror 21*b* and is transmitted downwardly toward the second sensor 22*b* The details of the transmission of energy through the fluid samples is described in more detail below.

The lasers 20 and the sensors 22 are optically coupled in a fixed orientation via the mirrors 21. In one embodiment, the laser(s) 20 are a visible wavelength collimated laser diode. In another embodiment, the laser(s) 20 deliver a laser beam from an optical fiber. In yet another embodiment, the laser(s) 20 include multiple wavelength sources from collimated laser diodes that are combined into a single co-boresighted beam through one of several possible beam combining methods. In yet a further example, the light source may be used that has an incoherent narrow wavelength source such as an Argon gas incandescent lamp that is transmitted through one or more pinholes to provide a beam of directionality. Each sensor 22 may include one or more the following devices—a camera, imager, calorimeter, thermopile, or solid-state detector array.

FIGS. 4 and 5 also illustrate the thermal control system for the instrument 10 that provides the incubation functionality. An infrared sensor 42 is located on the underside of the door platform 29 and measures the temperature of the rotatable platform 13 through the opening 35*d* on the door platform 29. One or more lamp heaters 44 are located on the base structure of the instrument 10. The heaters 44 create energy that is transmitted upwardly for warming the underside of the rotatable platform 13, thereby encouraging bacterial growth in the cuvettes. The energy is transmitted through the openings 35*b*, 35*c*, and 35*e* within the door platform 29 and is absorbed by the rotatable platform 13, which may have a dark lower surface for absorbing the energy.

A processor 50 is used to control the various aspects of the instrument 10 as will be described in more detail below with regard to FIG. 7. The instrument 10 includes an external systems interface 70 that allows for the instrument 10 to be connected to external systems. A port 80 associated with the external systems interface 70 allows for the direct connection to a special use computer that is used to control the instrument 10 and to receive information/data from the testing of the fluid samples. In addition to the display 28 located on the instrument 10 (and preferably the input buttons and/or touchscreen on the instrument 10), the instrument 10 communicates with an external device, such as a general purpose computer that would be coupled to a larger display that displays the output of the tests in tabular or graphical form. The instrument 10 can receive instructions from an external device that controls the operation of the instrument 10. The instrument 10 can also transmit data (e.g., forward-scatter signal data, test-protocol data, cuvette-assembly data derived from codes 62, as shown in FIG. 5, diagnostic data, etc.) from the port 30. The instrument 10 also includes an input power port (e.g., A/C power), which is then converted into a DC power supply for use by the motors, laser, sensors, and displays, etc.

FIGS. 4 and 5 also illustrate a reader 60 adjacent to the rotatable platform 13 for reading information from individual cuvettes or from a cuvette assembly 90. Because a cuvette assembly 90 may be used for different applications, the cuvette assembly 90 may include codes 62 (e.g., via QR code or a barcode) or RFID tags to identify the type of test supported by the particular cuvette assembly 90, as well as other measurement data to be taken. The instrument 10 preferably reads the RFID or barcode, and selects the software program stored in a memory device 55 (FIG. 7) to run the appropriate optical measurement tests on the cuvette assembly 90. Accordingly, the cuvette assembly 90 preferably includes an identification label that includes one or more barcodes and/or QR codes that provide the necessary coded information for the cuvette assembly 90. Other codes can be used as well.

When bacteria is a particle being checked within the liquid sample, one of the codes 62 may provide the protocol for the test (e.g., temperature profile over duration of test, frequency of the optical measurements, duration of test, etc.), and the processor 50 executes instructions from the memory 55 (FIG. 7) corresponding to the test protocol. Another one of the codes may be associated with information on the patient(s) from whom the liquid samples were taken, which may include some level of encryption to ensure that patient data is kept confidential. Another code may provide a quality-assurance check of the part number or the serial number for the cuvette assembly 90 to ensure that the cuvette assembly 90 is an authentic and genuine part, such that improper cuvettes are not tested. The code for the quality-assurance check may also prevent a cuvette assembly 90 from being tested a second time (perhaps after some type of cleaning) if it is intended for only single use. Again, the instrument 10 includes the device(s) 60 (such as an image sensor, a barcode reader/sensor, or a QR-code reader/sensor) to read the codes 62 on the assembly 90. Alternatively, the codes 60 on the label can be scanned as the assemblies 90 are placed onto the rotatable platform 13 (FIG. 5) such that the necessary information is obtained prior to the door 27 being closed.

FIG. 5 also illustrates the cuvette assembly 90 in its operational position after being loaded onto the rotatable platform 13 when the door 27 is opened. FIGS. 6A, 6B, and 6C illustrate the details of the cuvette assembly 90. The cuvette assembly 90 includes a plurality of fluid/optical chambers that are arranged in two circular (or arc-shaped) configurations. The outer circular configuration includes inner fluid chambers 92 positioned on a substantially circular locus. The cuvette assembly 90 includes outer fluid chambers 94 positioned on a substantially circular locus that has a larger radius than the substantially circular locus of the inner fluid chambers 92. As shown, the cuvette assembly 90 is comprised of seven individual cuvettes 91 (only six are shown in FIG. 6A) that are preferably disposable and used only once.

Alternatively, the cuvette assembly 90 can be comprised of a unitary annular-shaped structure, or two 180-degree cuvettes.

Each of the individual cuvettes 91 includes recesses 95 at its corners that allow the individual cuvettes 91 and, hence, the cuvette assembly 90 to be registered in the proper location on the rotatable plate 13 by the engagement of the recesses 95 with the registration posts 32 (see FIG. 5). Other types of physical registration features or, perhaps, magnetic elements may be used to register the cuvette assembly 90 on the rotatable plate 13. The registration of the cuvette assembly 90 on the rotatable platform 13 ensures that the inner fluid chambers 92 and the outer fluid chambers 94 are aligned with the openings in the registration platform 13. Accordingly, as the registration platform 13 undergoes its carousel-like motion under the power of the motor 31, the inner radial openings in the registration platform 13 and the inner fluid chambers 92 are sequentially positioned over the opening 35$f$ in the door platform 29 and the outer radial openings in the registration platform 13 and the outer fluid chambers 94 are sequentially positioned over the opening 35$a$ in the door platform 29. The openings 35$a$ and 35$f$ (and the mirrors 21 and sensors 22) are geometrically arranged to ensure that each time the motor 31 stops to align one outer fluid chamber 94 over the opening 35$a$, there is a generally opposing inner fluid chamber 92 aligned over the opening 35$f$. However, because there are more outer fluid chambers 94 than inner fluid chambers 92, one 360-degree cycle of testing the fluid chambers 92, 94 around the cuvette assembly 90 requires less testing (i.e., less sequential inputs from the laser 20$a$) of the inner fluid chambers 92 than the outer fluid chambers 94. In other words, in the illustrated embodiment, the laser 20$b$ is operational for forty-two tests of the forty-two outer fluid chambers 94 during a 360-degree rotation of the rotatable platform 13, while the laser 20$a$ is operational for only thirty-five tests of the thirty-five inner fluid chambers 92 during the same 360-degree rotation of the rotatable platform 13.

As shown best in FIGS. 6B and 6C, each of the fluid chambers 92 and 94 is bound at its upper and lower ends by an upper window 93$a$ and a lower window 93$b$, respectively. The upper window 93$a$ is formed on a top cover 96 that snaps onto a main body 97 of the cuvette 91. The upper window 93$a$ extends downwardly into the fluid chamber such that it is in contact with the fluid sample within the fluid chamber. The lower window 93$b$ is a thin layer (preferably made of optical grade plastic) that is attached to the lower portion of the main body 97. The lower window 93$b$ forms a bottom of the fluid chamber.

Each of the fluid chambers 92 and 94 includes multiple portions. The smaller portion 98 connects into a larger portion 99. In use, each of the fluid chambers 92 and 94 is filled with the fluid sample before the top cover 96 has been attached. Each of the fluid chambers 92 and 94 receives a known amount of fluid, such that, when the top cover 96 is attached to the main body 97, the upper window 93$a$ extends downwardly into the fluid chamber, contacts the fluid, and displaces the fluid in a manner that allows the fluid to move upwardly along the surface defining the smaller portion 98. Accordingly, the small portion 98 of each fluid chamber provides a spatial volume to accommodate the fluid displacement that occurs when the top cover 96 moves downwardly and the top window 93$a$ engages the fluid. During operation, the input beam enters the larger portion 99, which acts as an optical chamber, and the resultant forward-scatter signal exits from the lower window 93$b$. Each fluid sample may undergo some type of filtering within the cuvette assembly 90 (not shown) and/or outside the cuvette assembly 90 such that unwanted particles are substantially filtered, leaving only (or predominantly only) the bacteria.

To sequentially move the cuvette assembly 90 on the rotatable platform 13 in the operational mode, the motor 31 incrementally advances in a carousel-like fashion to align one outer fluid chamber 94 below the mirror 21$b$ and above the sensor 22$b$ so as to receive input energy from the laser 20$b$ that causes the forward-scatter signal. And when one of the outer fluid chambers 94 is so aligned, a corresponding one of the inner fluid chambers 92 on a generally opposing side of the cuvette 90 is aligned below the mirror 21$a$ and above the sensor 22$a$ so as to receive input energy from the other laser 20$a$. As such, two opposing fluid samples on the cuvette assembly 90 can be simultaneously tested or sequentially tested (with little or no time between sequentially firings of the lasers 20$a$ and 20$b$), and monitored via the corresponding forward-scatter signals. The circumferential spacing between adjacent outer fluid chambers 94 and inner fluid chambers 92 is selected to be a known circumferential distance that corresponds to predetermined number of rotational increments of the motor 31. In other words, as an example, if four increments of rotational movement of the motor 31 is known to create a 2-cm arc distance at a radius measured from the shaft of the motor 31 to the center points of the outer fluid chambers 94, then the center points for two adjacent outer fluid chambers 94 can be set at 2 cm in the design of the cuvette 90, knowing that four increments of operation of the motor 31 is needed to transition between adjacent outer fluid chambers 94.

The carousel-position sensor 33 (FIG. 3) located within the door platform 29 is used to sense the location of the rotatable platform 13 and, hence, the cuvette assembly 90.

The carousel position sensor 33 may include an encoder that is used to register the position of each of the inner and outer fluid chambers 92, 94 relative to the input beams of the lasers 20. Alternatively, the laser(s) 20 and sensor(s) 22 can be used for cuvette-orientation purposes if some of the openings within the rotatable platform 13 remain open (i.e., not covered by a cuvette) and sized in a way to provide a certain signal for the sensor(s) 22 to receive. As the rotatable platform 13 undergoes the carousel-like motion to begin the operational mode and register the first fluid chamber requiring testing, the lasers 20 and corresponding sensors 22 can identify the circumferential location of the first fluid chamber by identifying these unused and differently sized openings within the rotatable platform 13 as it rotates. The processor 50, upon receiving the signal output from the sensors 22, then selectively controls the motor 31 to place the first fluid chamber to be tested in the appropriate circumferential position under one of the input beams reflected from the mirror 21a or 21b.

Figure 6D:
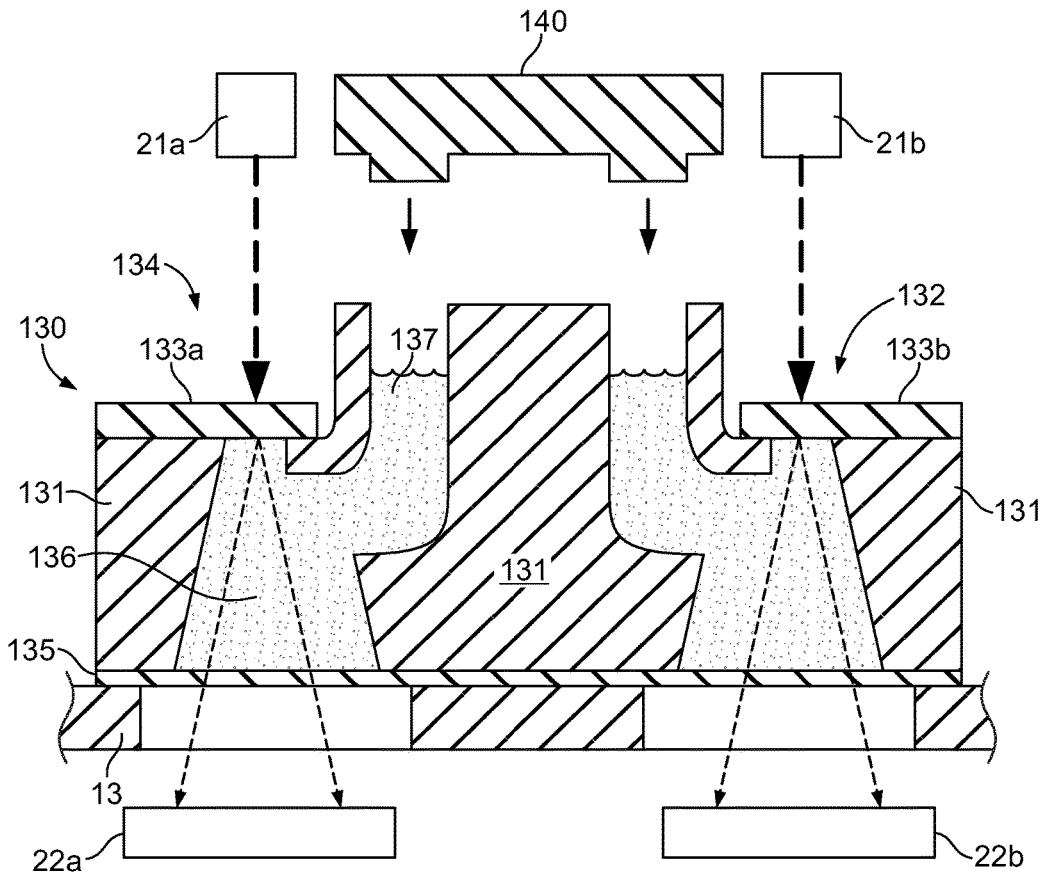
FIG. 6D is a cross-sectional view through the main body of an alternative cuvette assembly that fits on the rotational platform of the instruments of FIGS. 1-5.

FIG. 6D illustrates an alternative embodiment of a cuvette 130, which could be annular-shaped like the cuvette assembly 90 or arc-shaped like the individual cuvette 91 in FIGS. 6A-6C. The cuvette 130 is shown in cross-section through the main body 131 in the region of a single inner fluid chamber 132 and a single outer fluid chamber 134, although the cuvettes 130 would have numerous inner fluid chambers 132 and outer fluid chambers 134 (e.g., forty-two outer fluid chambers 134 and thirty-five inner fluid chambers 132). An upper window 133a is attached to the main body 131 in the region of the outer fluid chamber 134, while an upper window 133b is attached to the main body 131 in the region of the inner fluid chamber 132. Each of the upper entry windows 133a and 133b may be annular shaped (or arc-shaped) such that it fits entirely (or partially) around the cuvette 130 (e.g., the window 133a is a unitary piece of optical grade plastic that covers all of the outer fluid chambers 134 and the window 133b is a separate unitary piece of optical grade plastic with a slightly smaller radius that covers all of the inner fluid chambers 132). A lower exit window 135 is also attached to the main body 131 and, as illustrated, is a unitary piece of optical grade plastic that covers the bottom of all of the inner fluid chambers 132 and the outer fluid chambers 134. Individual entry windows 133 and exit windows 135 can be used as well. The cuvette 130 is shown resting on the rotatable platform 13, which has openings aligned with all of the inner fluid chambers 132 and the outer fluid chambers 134, as noted above with respect to FIGS. 6A-6C.

Each of the inner fluid chambers 132 and the outer fluid chambers 134 includes a main volume 136 for holding the fluid sample during the tests in which the input beam from the laser 20 reflects off the mirror 21, transmits through the fluid sample, and creates a forward scatter signal that is received by the sensor 22. Directly adjacent to the main volume 136 is a fluid input port 137 extending upwardly above the overall height of the main volume 136 to ensure that sample fluid that is received within each of the fluid chambers will engage the lower surface of the upper window 133. Accordingly, by having the fluid input port 137 located above (relative to the gravitational gradient) the upper window 133, the fluid sample should completely fill the main volume 136 under gravity without bubbles, which can be problematic for operation. During operation, the input beam enters the main volume 136, which acts as an optical chamber, and the resultant forward-scatter signal associated with the bacterial concentration (or other particles in the fluid) exits from the lower window 135 and passes through an opening in the rotatable table 13. The cuvette 130 may also include a cap 140 having resilient lower bosses that fit within each of the fluid input ports 137 of the inner fluid chambers 132 and the outer fluid chambers 134 to seal the cuvette 130 after its chambers have been filled. The cap 140 can be annular-shaped or arc-shaped, depending on the overall shape of the cuvette 130.

Figure 6E:
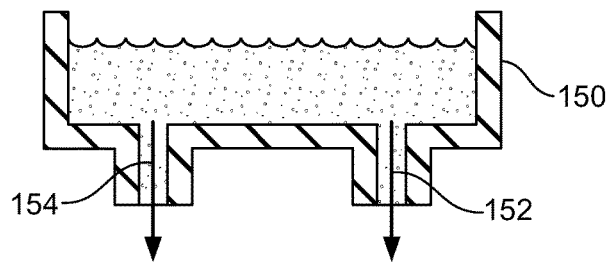
FIG. 6E is a cross-sectional view a bulk fluid-loading manifold that is used with the alternative cuvette of FIG. 6D.

FIG. 6E illustrates one example of a fluid-input manifold 150 that can be used to simultaneously fill all of the inner fluid chambers 132 and the outer fluid chambers 134 with a single type of fluid sample. The fluid-input manifold 150 includes a series of inner fluid channels 152 and a series of outer fluid channels 154. The inner fluid channels 152 are designed to fit within the fluid input ports 137 of the inner fluid chambers 132. The outer fluid channels 154 are designed to fit within the fluid input ports 137 associated with the outer fluid chambers 134. After the fluid input manifold 150 has been installed onto the cuvette 130, a known amount of fluid that is needed to collectively fill all of the inner fluid chambers 132 and outer fluid chambers 134 in the cuvette 130 can be filled into the upper portion of the manifold 150, such that the sample fluid simultaneously fills each of the inner fluid chambers 132 and the outer fluid chambers 134 within the cuvette 130. To ensure that the fluid amount does not rise to the top of each of the fluid input ports 137, the amount of material that is used to create each of the inner fluid channels 152 and 154 (which extend into the fluid input ports 137) can be tailored so as to create a known non-fluid volume within each fluid entry port 137. After the removal of the manifold 150 from the cuvette 130 after the filling process is complete, there is added volume created within each fluid entry port 137 to receive the sample fluid, resulting in the upper surface of the sample fluid within each inner input port 137 falling below the upper surface of the main body 131. The cap 140 can then be placed over each of the fluid input ports 137, as described above with reference to FIG. 6D. The manifold 150 may have a closed top with a needle-free swabable port valve for receiving a known volume of fluid. In this arrangement, the inner fluid chambers 132 and the outer fluid chambers 134 of the cuvette 130 can be individually loaded (e.g., when numerous different fluid samples tested), or they can be "bulk" loaded with a single fluid sample by use of the manifold 150.

Figure 7:
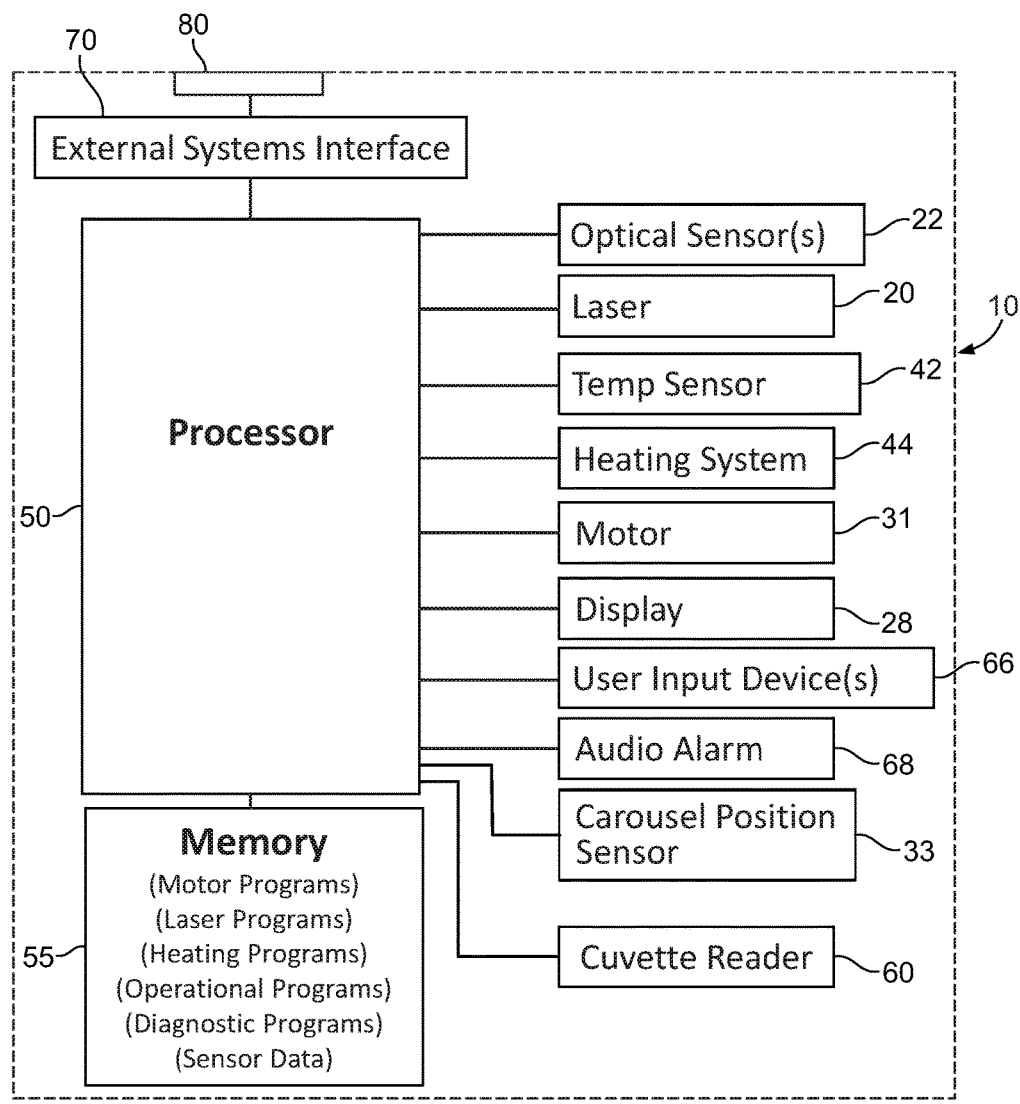
FIG. 7 illustrates a system control diagram for the instruments of FIGS. 1-5.

FIG. 7 illustrates one embodiment for a control system that is located within the instrument 10. The instrument 10 includes one or more printed circuit boards that include at least one processor 50 (and possibly several processors) and at least one memory device 55. The processor 50 communicates with the memory device 55, which includes various programs to operate the motor(s), the laser, the sensors, the heating system, the basic operational functionality, diagnostics, etc. The processor 50 is in communication with the functional components of the instrument 10, such as (1) the optical sensors 22a and 22b that sense the forward-scatter signals (or other optical signals, such as fluorescence signals), (2) the lasers 20 or other light source that creates the light beam is transmitted into the cuvettes, (3) temperature sensor(s) 42 that determines the temperature of the rotatable plate 13 or within the housing 25 (or associated with the surface of the cuvette), (4) the heating system 44, which includes the heater lamps and/or the other heating elements, (5) the motors 31 used for rotating the platform 13, (6) the display(s) 28 on the front of door 27 of the instrument 10, (7) any user input devices 66 (mechanical buttons or touch-screens), (8) an audio alarm 68 to alert the operator of the instrument 10 to a particular condition or event (e.g., to indicate that one or more samples have reached a certain testing condition, such as a high bacterial concentration, a certain slope in a bacterial-growth curve has been achieved, or a certain forward-scatter signal exceeds a certain value), (9) the carousel-position sensor 33 on the door platform 29, and (10) the cuvette reader 60 for reading codes that provide information regarding the cuvettes, the testing protocol, etc.

The processor 50 is also communicating with an external systems interface 70, such as interface module, associated with the output port 80 on the instrument 10. The primary functions of the processor(s) 50 within the instrument 10 are (i) to maintain the enclosure within the instrument 10 at the appropriate temperature profile (temperature versus time) by use of the temperature sensors 42 and heating system 44, (ii) to sequentially actuate the lasers 20a and 20b so as to provide the necessary input beam into the samples within the cuvette assembly 90, (iii) to controllably rotate the platform 13 via the motor 31 and the carousel-position sensor 33 to ensure proper alignment of the input beam and the chamber containing the fluid sample, (iv) to receive and store/transmit the data in the memory device 55 associated with the optical (e.g., forward-scatter) signals from the sensors 22a and 22b, and (v) possibly, to analyze the forward-scatter signals to determine the bacterial concentration. Alternatively, the control system or computer module that controls the instrument 10 could be partially located outside the instrument 10. For example, a first processor may be located within the instrument 10 for operating the laser, motors, and heating system, while a second processor outside the instrument 10 handles the data processing/analysis for the forward-scatter signals received by the sensors 22a and 22b to determine bacterial concentration. The test results (e.g., bacterial concentration indication) and data from the instrument 10 can be reported on the instrument display 28 and/or transmitted by USB, Ethernet, wifi, Bluetooth, or other communication links from the external systems interface 70 within the instrument 10 to external systems that conduct further analysis, reporting, archiving, or aggregation with other data within a network. In one preferred embodiment, a central database receives test results and data from a plurality of remotely located instruments 10 such that the test data and results (anonymous data/results) can be used to determine trends using analytics, which can then be used to derive better and more robust operational programs for the instrument 10 (e.g., to decrease time per test, or decrease the energy of the tests by used lower incubation temperatures).

The instrument 10 in FIGS. 1-7 uses laser-scattering technology to quantify bacteria growth in fluid sample sizes that are smaller than 0.5 ml, and preferably about 0.1 ml. Each of the fluid chambers 132, 134 provides enough vertical height (e.g., about 10 mm to 12 mm) to cause the desired interaction of the laser beam with the bacteria to produce the forward scatter signal. The upper entry windows preferably are more than twice the diameter of the input beam, which is usually less than 1 mm, and preferably between about 0.5 mm and 0.75 mm. Hence, the upper windows have a diameter in the range from about 2 mm to 2.5 mm. The divergence of the input beam as it passes through the fluid sample is within about 8° as measured from the central axis, such that the exit windows typically have a diameter in the range from about 4 mm to 5 mm. The volume and shape of the fluid chambers is also configured to minimize bubbles. In particular, the instrument 10 transmits a beam from each laser 20a, 20b through a fluid sample, and measures the scatter signal at the sensors 22a, 22b caused by the bacteria in the fluid sample, preferably through a forward-scattering measurement technique. The on-board incubation through the heating system 44 and temperature sensor 42 provides for fluid sample temperatures ranging from room temperature up to 42° C. (or higher). The instrument 10 permits for a range of optical measurement intervals over a period of time (e.g., 1-6 hours) to determine the growth and concentration of the bacteria within the liquid samples during incubation. The optical measuring instrument 10 can detect and count bacteria by various techniques that are generally described in U.S. Pat. Nos. 7,961,311 and 8,339,601, both of which are commonly owned and are herein incorporated by reference in their entireties.

Due to the incubation feature within the instrument 10, the necessary environment around the cuvette assemblies 90 can be controlled to promote the growth of the bacteria, such that subsequent optical measurements taken by the combination of the lasers 20a and 20b and the sensor 22a and 22b results in a stronger forward-scatter signal indicative of increased bacterial concentration. The instrument 10 includes internal programming that (i) controls the environment around the fluid sample and (ii) dictates the times and/or times-intervals between optical measurements to determine whether the bacteria has grown and, if so, how much the concentration of bacteria has increased. The real-time output from the instrument 10 can be seen on a separate display coupled to the port 80.

In one mode of operation of the instrument 10, the fluid samples in the cuvette assembly 90 (or each individual cuvette 91) is from a single sample (e.g., from a single patient) Each of the fluid chambers 92 and 94 could be pre-loaded with a certain chemoeffector (different types and different amounts of each type) including a drug, antimicrobial agent, nutrient, chemical tag or colorant. Each optical chamber is then sequentially measured with one or more optical beam lines, or by moving the fluid samples through the input beam lines below the mirrors 22. If each individual optical chamber includes a different chemoeffector (e.g., different dosage of an antibiotic), then the effect of the separate chemoeffector can be monitored over time for a single fluid sample. Thus, the instrument 10 in can be used to determine the effects of a chemoeffector (a drug, antimicrobial agent, nutrient, chemical tag or colorant) on a single sample if the cuvette assembly 90 (or individual cuvette 91) is loaded with a sample from a single patient, but the chambers includes different chemoeffectors. In this scenario, the instrument 10 may test a single patient's sample against multiple chemoffectors. As such, the measurement instrument 10 in conjunction with the cuvette assembly 90 can be used to determine the effects of a chemoeffector (e.g., a drug, antimicrobial agent, nutrient, chemical tag or colorant) on a single sample if the cuvette (such as cuvettes assembly 90 or individual cuvettes 91) is loaded with a single sample (e.g., from a single patient), but the optical chambers includes different chemoeffectors (or each the seven cuvettes 91 in the cuvette assembly 90 is designed to test a single chemoeffector eleven times via the eleven fluid chambers 92, 94 for accuracy/repeatability). The codes 62 on the label on the cuvettes 91 of the assembly 90 may identify which chemoeffector is being tested within the respective cuvette 91.

Figure 8:
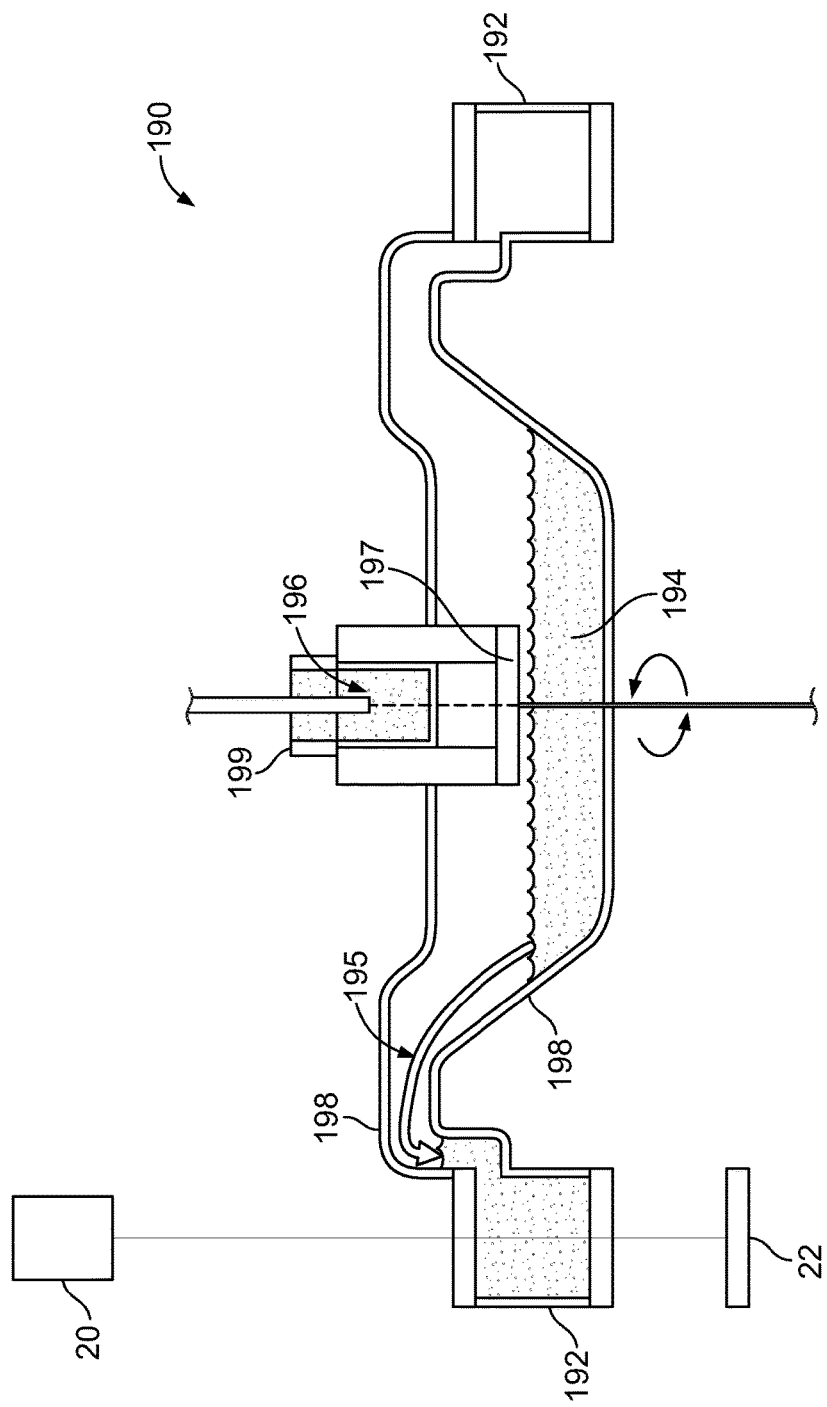
FIG. 8 is a cross-sectional view through the main body and two opposing fluid chambers of an alternative cuvette assembly that fits on the rotational platform of the instruments of FIGS. 1-5.

FIG. 8 illustrates a different rotatable cuvette assembly 190 for the instrument 10 in which a single sample is constituted from one or multiple liquids and/or dry materials that are combined and mixed. The cuvette assembly 190 includes a port 196 for addition of these materials, and a central chamber 194 for mixing of materials. Filters 197 may be used to minimize the particles that are transferred into the central mixing chamber 194. The rotatable cuvette assembly 190 includes an arrangement of a plurality of measurement chambers 192 (e.g., cuvettes) configured around the central chamber 194 with passages or channels 195 defined by walls 198 for communicating the liquid from the central mixing chamber 190 to the peripheral measurement chambers 192. The cuvette 190 may have several peripheral measurement chambers 192 (e.g., thirty or forty) arranged around the central chamber 194 in ways to permit the use of both lasers 20a and 20b and sensors 22a and 22b. The passages 195 may be configured above the intended fill level of the central mixing chamber 194 and could be sloped such that rotation of the assembly 190 would centrifugally force liquid up to the passages 195 and then into the peripheral measurement chambers 192. Alternatively or additionally, valves or seals within the passages 195 could be configured to preclude flow to the measurement chambers until satisfactory mixing is completed. The port 196 may be coupled to a needle-free swabble input valve 199 to eliminate or inhibit dripping of the sample fluid as the cuvette assembly 190 is being loaded.

The central mixing chamber 194 and the peripheral measurement chambers 192 can be made of a disposable plastic material, such that they are used for only a single sample. Similarly, the walls 195 defining the passages 198 can be made of a similar plastic material. In one embodiment, a single disposable unit would include a spider-like configuration having the central chamber, the passages/channels, and the peripheral measurement chambers, all of which snap into (or fit within) corresponding structures (e.g., registration posts 32) of the rotatable platform 13 of the instrument 10 that provides for the rotational movement and optical sensing.

In an additional embodiment, each of the peripheral measurement chambers 192 could be pre-loaded with a chemoeffector including a drug, antimicrobial agent, nutrient, chemical tag or colorant. The single fluid sample can be constituted in the central chamber 194, mixed by rotation of the chamber (perhaps assisted by vanes or paddles in the central chamber), and then centrifugally distributed to the peripheral measurement chambers 192 by spinning of the assembly 190. Each peripheral measurement chamber 192 is then sequentially measured by rotation of the assembly 190 to move the individual measurement chambers 190 into position with one or more optical beam lines defined between with the laser 20 (or mirror 21) and the sensor 22. Alternatively, a different instrument may move the beamlines around the sample assembly 190. If each individual measurement chamber includes a different chemoeffector (e.g., different dosage of an antibiotic), then the effect of the separate chemoeffector can be monitored over time.

To the extent the fluid samples require mixing or agitation, the rotatable platform 13 may be equipped with a vibration-producing mechanism to help agitate the samples in the cuvette assembly 90. For example, the motor 31 can be operated in mode whereby it repetitively moves the cuvette assembly 90 back-and-forth to provide the necessary mixing.

In yet another embodiment of the instrument 10, the light source 20 and the sensor 22 are fixed, and the multiple sample chambers are fixed as well. However, optical elements such as mirrors or prisms on electro-mechanical actuators are used to move the light beam from measurement chamber to measurement chamber within each sample. Hence, the electro-mechanical actuators and possibly motors are used to move the light beam, while the light source, the sensor(s), and the multiple sample chambers are fixed. A single light beam source can also be split into multiple input beams used with the mirrors 22a and 22b.

Regarding the measurement of bacteria, the instrument 10 preferably measures bacteria and other organisms generally in the range for 0.1 to 10 microns with a measurement repeatability of 10%. The instrument 10 can measure a low concentration of $1 \times 10^4$ cfu/ml (based on E-coli in filtered saline) and deliver continuous measurements showing growth beyond $1 \times 10^9$ cfu/ml. The instrument 10 can be loaded with factory-set calibration factors for approximate quantification of common organisms. Further, the user can load custom calibration factors with specific test protocols for use with less common organisms or processes.

Considering that the particles in the fluid (especially bacteria) may be in motion, it is possible that large clusters may affect the forward-scatter signal on any given test sample. Accordingly, in one preferred embodiment, multiple consecutive test data points for each fluid sample are averaged to avoid having a single forward-scatter signal with a large cluster of particles or a single forward-scatter signal corresponding to only a few particles affect the overall test results. In one example, five consecutive forward-scatter signal test data points are averaged under a rolling-average method to develop a single average signal. Thus, as a new data point is taken for each sample, it is used with the previous four data points to develop a new average. More or less data points than five can be used for this rolling average. Further, the computation methodology may use various algorithms to remove the high and low signals (or certain ultra-high or ultra-low signals) before taking the average. Or, the computation methodology can be as simple as choosing the mathematical median of a data set. Ultimately, the forward-scatter signals from the instrument 10 will produce a bacterial-growth curve having a certain slope over a period of time at an appropriate incubation temperature.

Generally, growth curves are numerically filtered and analyzed for determination of initial concentration, growth percentage for a predefined period of time, and changes in the growth rate. Determination of bacterial absence or bacterial presence above a predefined threshold is based on a combination of those parameters with thresholds that are characteristic for bacterial growth and salts crystallization/dissolving kinetics. In one basic example, if the slope is above a predetermined value, the patient's sample is infected. Alternatively, it could be that the slope that indicates the presence of an infection may be different for different periods of time (e.g., $Slope_{infection} > X$ within T=0 to 30 minutes; $Slope_{infection} > 1.5X$ within T=30 to 60 minutes; etc.)

Particles with a refractive index different from the surrounding medium will scatter light, and the resultant scattering intensity/angular distribution depends on the particle size, refractive index and shape. In situations in which the input light is scattered more than one time before exiting the sample (known as multiple scattering), the scattering also depends on the concentration of particles. Typically, bacteria have a refractive index close to that of water, indicating they are relatively transparent and scatter a small fraction of the incident beam, predominantly in the forward direction. With the optical design within the instrument 10, it is possible to look at scattering angles down to about 2° without having the incident input beam or other noise signals (e.g., the scattering from the cuvette windows) interfere with light scattered by bacteria. By simultaneous measurement of the forward scattering and optical density, measurements could be extended down to $10^{-5}$, allowing accurate measurement of concentrations as low as $10^3$ CFU/mL.

Optical density measurements are intended to determine sample concentrations that are not accurate, as the size of the scattering particles greatly affects the resulting optical density. A similar optical density is obtained for samples with a few large size bacteria in comparison with a higher concentration of small size bacterial samples. Moreover, additional calibration of the optical density to concentration does not render more accurate results, since the size changes during the bacterial growth process.

It is also possible to use the instrument 10 to measure the number of bacteria within the fluid sample. By use of the Mie scattering model for spherical particles and the T-matrix method of light scattering, combined with Monte-Carlo ray tracing calculation that takes into account multiple scattering, it is possible to evaluate the number of bacteria and their size from the measurement of the optical density and the scattered light angular distribution.

The results are nearly independent of the specific particle shape and loosely depend on the size dispersion of bacteria, resulting in a small constant shift of the mean size. Thus, both bacterial concentration and size are evaluated from the measured parameters by a first principle model without any free parameters, except the bacteria refractive index, that is measured by calibration for each of the bacteria species. In short, the instrument 10 can be used to detect forward scatter signals corresponding to scattering intensity and angular distribution (e.g., for angles less than 5°, such as angles down to about 2°) and also the optical density of the fluid samples, which can then be evaluated to determine the number of bacteria and their sizes (and changes to the number of bacteria and to their sizes over a period of time).

The system and method associated with FIGS. 1-8 have various uses and applications. For example, in the area of research, it can be used for (i) microbial concentration and grow analyses, (ii) quantification of antimicrobial, antibiotics, and environmental effects, and (iii) antibiotic drug development and clinical trial enrollment. In the area of hygiene and safety, it can be used for (iv) antimicrobial and antibiotics quality assurance testing, (v) process and potable water testing, and (vi) surface, wipe, and swab microbial testing. In the area of clinical microbiology for humans and animals, it can be used for (vii) rapid detection and quantification of infection, (viii) rapid antibiotic susceptibility testing (AST), (ix) drug-testing and measurement, and (x) antibiotic sensitivity testing for quality control.

The present invention associated with FIGS. 1-8 also contemplates the identification (or partial identification) of the type of bacteria that is present in fluid sample. For example, if a certain type of fluid is known to have a limited number of types of bacteria, one type of bacteria may be known to grow at a fast rate at a certain incubation temperature relative to the other bacteria, leading to a higher slope on the growth curves. One type of bacteria may be known to grow at a slower rate at a certain incubation temperature relative to the other bacteria, leading to a lower slope on the growth curves. Or a group of bacteria may be known to have certain growth curves, leading to the partial identification by eliminating the other types of bacteria that may be possibly present in the fluid sample. Using multiple instruments 10 with the same set of fluid samples but at different incubation temperatures (e.g., the same samples in three instruments 10 at 38° C., 40° C., and 42° C.) can result in different bacterial-growth curves, which identify one type of bacteria relative another (or at least a species of bacteria). Further, if one bacteria (or a species of bacteria) are known to die above a certain temperature, then after the samples have been tested, the instrument 10 can ramp-up the temperature to see if the growth curve flattens for any sample, indicating that the sample may be infected by the bacteria that is known to die above the operating temperature.

In a further example, complex UTI cases in humans are known to have both Gram Positive bacteria and Gram Negative bacteria. Crystal Violet is a dye that adheres to the rough surface of Gram Positive bacteria and, in the process, causes the pores on the surface to become "clogged" so as to kill the Gram Positive bacteria. Therefore, inclusion of Crystal Violet in one or more fluid chambers 92, 94 of the cuvette assembly 90 while other chambers in the cuvette assembly 90 lack it permits identification of the UTI infection type. If the bacteria growth curve continues similarly in both chambers, then the patient's sample is likely infected by only a Gram Negative bacteria. On the other hand, if the bacteria growth curve in the chamber having Crystal Violet has a substantially smaller slope, then the infection likely includes a Gram Positive bacteria. As such, at least a partial identification of the bacteria has been achieved. In this case, the chemoeffector is an inert chemistry (Crystal Violet) that impacts the growth behavior of the organisms, and by comparison to a control, some identification information for the bacteria can be obtained.

Each of these embodiments and obvious variations thereof is contemplated as falling within the spirit and scope of the claimed invention, which is set forth in the following claims. Moreover, the present concepts expressly include any and all combinations and subcombinations of the preceding elements and aspects.

The invention claimed is:

1. An optical measuring instrument for determining a concentration of bacteria in a plurality of fluid samples, comprising:
   a housing;
   a rotatable platform within the housing;
   a plurality of fluid containers coupled to the rotatable platform, each of the fluid containers holding a corresponding one of the plurality of fluid samples, each of the fluid containers having an input window and an output window;
   a light source within the housing for providing an input beam for transmission into the input windows of the fluid containers and through the corresponding fluid samples, wherein the input window and the output window are vertically arranged with the fluid sample located therebetween,
   a first mirror mounted to reflect the input beam in a vertical direction through the input window, the input beam creating a forward-scatter signal associated with the concentration of bacteria;
   a motor for rotating the rotatable platform so that the input beam sequentially passes through each of the plurality of fluid samples; and
   at least one sensor within the housing below the rotatable platform optically coupled to the light source in fixed orientation to the mirror, for detecting the forward-scatter signal exiting from the output window associated with the fluid sample receiving the input beam for analysis of bacteria in the fluid sample.

2. The optical measuring instrument of claim 1, further including a heating system within the housing to maintain the fluid samples at a desired temperature to encourage bacterial growth in the fluid samples over a period of time.

3. The optical measuring instrument of claim 2, wherein the heating system includes a plurality of heat lamps that provide energy to a bottom surface of the rotatable platform, a top surface of the rotatable platform receiving the plurality of fluid containers.

4. The optical measuring instrument of claim 1, wherein the plurality of fluid containers are a part of a cuvette, the cuvette having an arc-shape and being registered on the rotatable platform.

5. The optical measuring instrument of claim 1, wherein the rotatable platform has a plurality of openings that are aligned with the output windows of the cuvette.

6. The optical measuring instrument of claim 1, wherein the plurality of fluid containers include at least one of (i) a single chemoeffector at different concentrations and (ii) different chemoeffectors, the plurality of fluid samples being derived from the same fluid sample source to determine the effects of the chemoeffector on the bacterial concentration of the respective fluid sample.

7. The optical measuring instrument of claim 1, further comprising a second light source within the housing for providing a second input beam for transmission into the input windows of the fluid containers and though the corresponding fluid samples, the second input beam creating a forward-scatter signal associated with the concentration of bacteria, the light source for measuring a first group of the fluid samples and the second light source for measuring a second group of the fluid samples.

8. The optical measuring instrument of claim 7, wherein the plurality of fluid containers are contained in a cuvette, the first group of the fluid samples being located in the cuvette on first locus have a first radius, the second group of the fluid samples being located in the cuvette on second locus have a second radius, the first radius being different from the second radius.

9. The optical measuring instrument of claim 1, further comprising a door coupled to the housing, the door including a door platform that extends inwardly into the housing when the door is positioned in a closed state.

10. The optical measuring instrument of claim 1, further comprising:
a second light source for providing a second input beam for transmission into the input windows of the fluid containers and through the corresponding fluid samples; and
a second mirror for turning the second input beam toward the input windows of the fluid containers.

11. The optical measuring instrument of claim 1, wherein each of the plurality of fluid containers incudes a plurality of optical chambers and a plurality of fluid-input ports for filling the plurality of optical chambers, each of the fluid-input ports having an opening positioned, with respect to gravity, above the input and output windows for the respective optical chamber.

12. The optical measuring instrument of claim 11, wherein each of the plurality of fluid containers includes a main body and a top cover, the input window for each of the plurality of optical chambers being located on the top cover, the plurality of optical chambers being located in the main body, the top cover being initially removed from the main body to permit the filling of the optical cavities with the plurality of fluid samples, the top cover being attachable to the main body after the plurality of fluid samples are filled within respective ones of the optical chambers.

* * * * *